(12) United States Patent
Hirata et al.

(10) Patent No.: US 10,816,500 B2
(45) Date of Patent: *Oct. 27, 2020

(54) GAS SENSOR, METHOD FOR PRODUCING CONDUCTIVE PASTE, AND METHOD FOR MANUFACTURING GAS SENSOR

(71) Applicant: NGK INSULATORS, LTD., Nagoya-shi, Aichi (JP)

(72) Inventors: Noriko Hirata, Nagoya (JP); Taku Okamoto, Nagoya (JP); Yuki Nakayama, Nagoya (JP); Osamu Nakasone, Inabe (JP)

(73) Assignee: NGK INSULATORS, LTD., Nagoya (JP)

( * ) Notice: Subject to any disclaimer, the term of this patent is extended or adjusted under 35 U.S.C. 154(b) by 227 days.

This patent is subject to a terminal disclaimer.

(21) Appl. No.: 15/347,886

(22) Filed: Nov. 10, 2016

(65) Prior Publication Data

US 2017/0138891 A1   May 18, 2017

(30) Foreign Application Priority Data

Nov. 17, 2015 (JP) .................. 2015-224648
Apr. 15, 2016 (JP) .................. 2016-082212

(51) Int. Cl.
  *G01N 27/407*   (2006.01)
  *G01N 33/00*    (2006.01)
  *G01N 27/30*    (2006.01)

(52) U.S. Cl.
  CPC ....... *G01N 27/4071* (2013.01); *G01N 27/301* (2013.01); *G01N 27/4073* (2013.01); *G01N 27/4074* (2013.01); *G01N 27/4075* (2013.01); *G01N 33/0047* (2013.01)

(58) Field of Classification Search
  None
  See application file for complete search history.

(56) References Cited

U.S. PATENT DOCUMENTS

| 4,207,159 | A  | * | 6/1980  | Kimura .............. G01N 27/4065 204/425 |
| 6,153,072 | A  |   | 11/2000 | Inoue et al. |
| 8,133,370 | B2 |   | 3/2012  | Roessler et al. |
| 8,366,893 | B2 |   | 2/2013  | Fujisaki et al. |

(Continued)

FOREIGN PATENT DOCUMENTS

| JP | 3566089 B2 | 6/2004 |
| JP | 4405643 B2 | 11/2009 |

(Continued)

*Primary Examiner* — Gurpreet Kaur
*Assistant Examiner* — Steven E Rosenwald
(74) *Attorney, Agent, or Firm* — Global IP Counselors, LLP

(57) ABSTRACT

A gas sensor capable of measuring a high concentration range is provided. A sensing electrode provided in a sensor element of a mixed-potential gas sensor for measuring the concentration of a predetermined component in a measurement gas is formed of a cermet including a noble metal and an oxygen-ion conductive solid electrolyte. The noble metal includes Pt and Au. A Au abundance ratio, which is an area ratio of a portion covered with Au to a portion at which Pt is exposed in a surface of noble metal particles forming the sensing electrode, is 0.1 or more and less than 0.3.

12 Claims, 6 Drawing Sheets

(56) References Cited

U.S. PATENT DOCUMENTS

2002/0023838 A1* 2/2002 Schneider .......... G01N 27/4071
                                                     204/429
2010/0243447 A1* 9/2010 Fujisaki ............. G01N 27/4075
                                                     204/431

FOREIGN PATENT DOCUMENTS

JP         4914447 B2    1/2012
JP         5323752 B2    7/2013

* cited by examiner

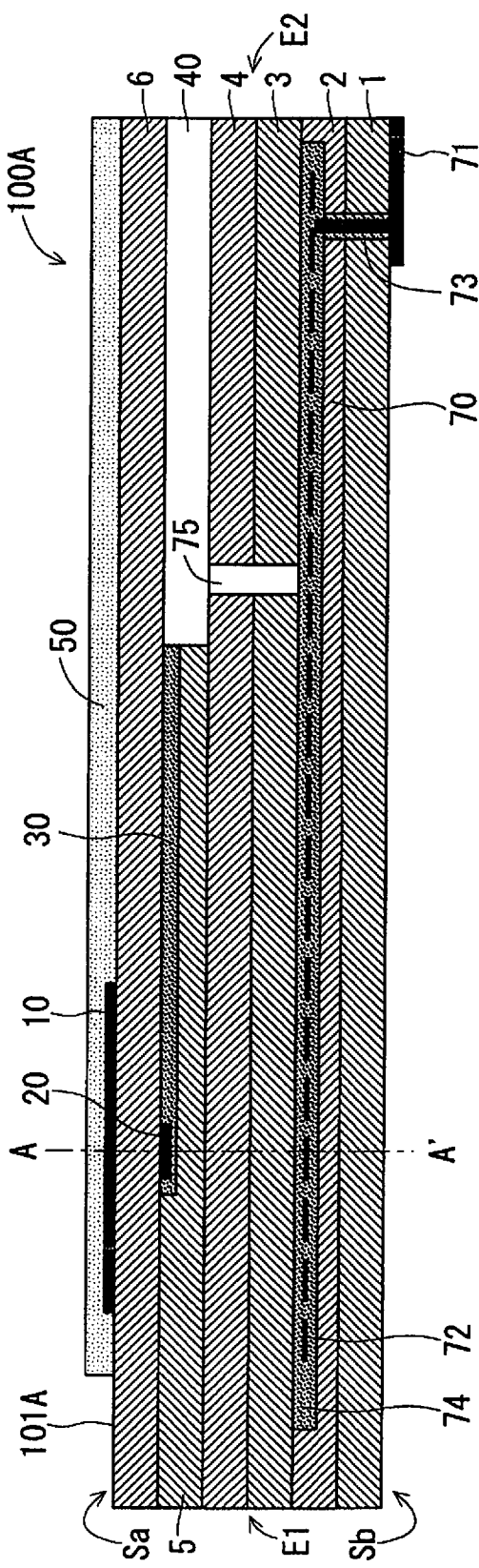

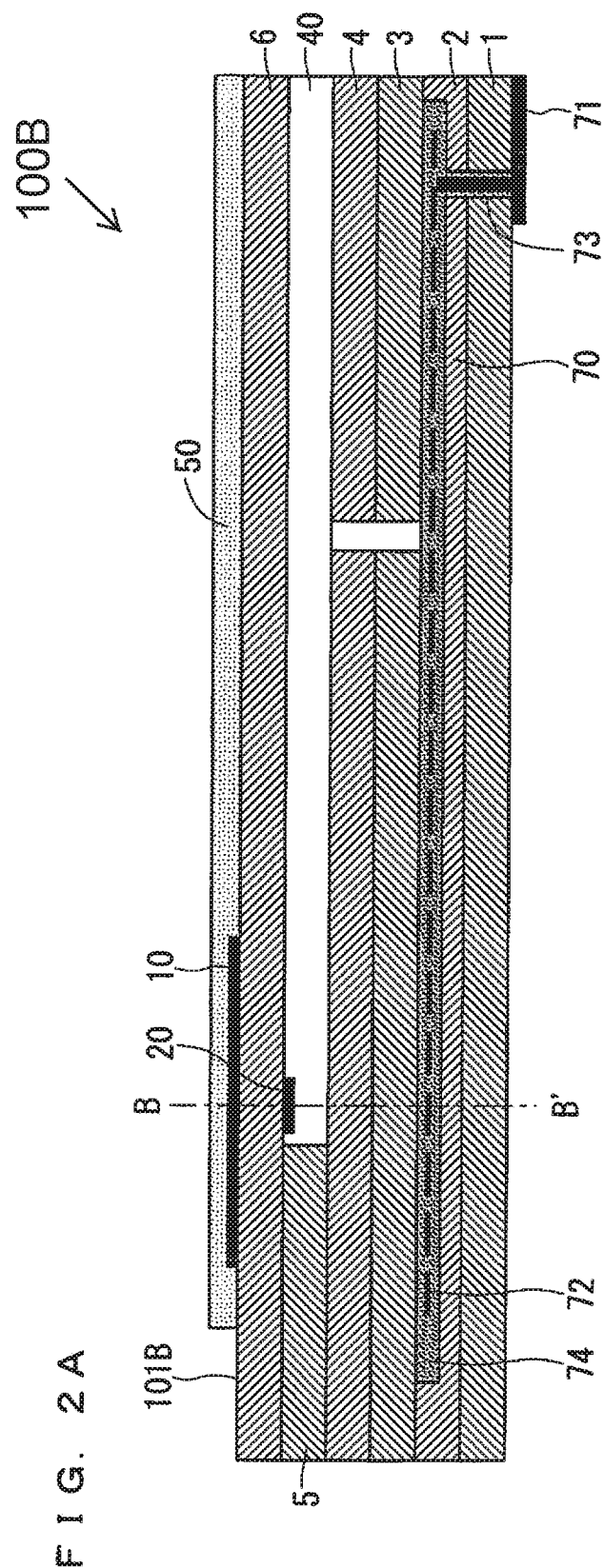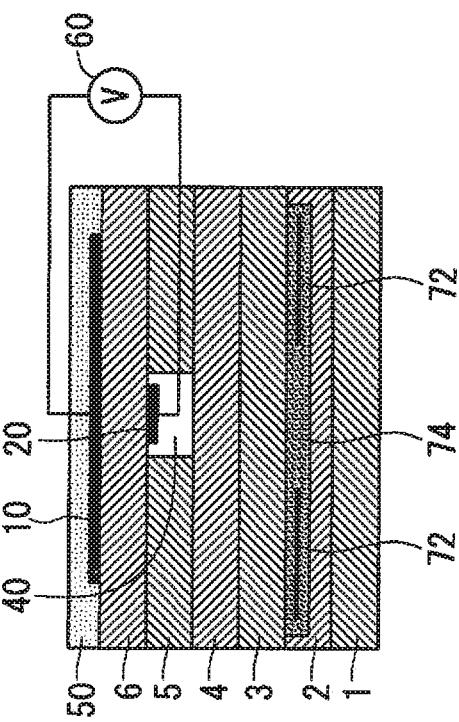

GAS SENSOR, METHOD FOR PRODUCING CONDUCTIVE PASTE, AND METHOD FOR MANUFACTURING GAS SENSOR

BACKGROUND OF THE INVENTION

Field of the Invention

The present invention relates to a gas sensor for sensing a predetermined gas component of a measurement gas, and more particularly, to a sensing electrode of the gas sensor.

Description of the Background Art

Gas sensors that sense a predetermined gas component of a measurement gas to determine its concentration come in various types such as a semiconductor gas sensor, a catalytic combustion gas sensor, an oxygen-concentration difference sensing gas sensor, a limiting current gas sensor, and a mixed-potential gas sensor (for example, see Japanese Patent Nos. 4405643, 4914447, 3566089, and 5323752). Some of these gas sensors are obtained by providing electrodes containing a noble metal as its main constituent to a sensor element mainly made of ceramic that is a solid electrolyte such as zirconia.

Japanese Patent No. 4405643 discloses a gas sensor provided with a thin layer mainly made of Pt or Au to compensate for the adhesion between a solid electrolyte and an electrode made of metal oxide and gold.

Japanese Patent No. 4914447 discloses a mixed-potential gas sensor including a first electrode formed through application of a Pt—Au paste and a second electrode formed through application of a Pt paste and Au plating.

Japanese Patent Nos. 3566089 and 5323752 disclose a limiting current gas sensor including a sensor element formed of solid electrolyte, which includes electrodes made of Pt—Au alloy as pumping electrodes.

In response to more stringent regulations on exhaust gas, there have recently been increasing demands for a diagnosis of failure in the performance of cleaning unburned hydrocarbon in an exhaust emission control system (TWC: three-way catalyst) of a gasoline engine and a diagnosis of failure in the performance of cleaning unburned hydrocarbon in an exhaust emission control system (DOC: diesel oxidation catalyst) of a diesel engine. These diagnoses require a gas sensor capable of sensing an unburned hydrocarbon gas and identifying its concentration.

The inventors of the present invention have made intensive studies to find out that in a sensing electrode made of Pt—Au alloy having an increased Au abundance ratio, a catalytic activity against a hydrocarbon gas is disabled, inducing a mixed potential having correlation with the concentration of the hydrocarbon gas. Such finding has led the inventors to a gas sensor capable of sensing a hydrocarbon gas with high sensitivity.

Japanese Patent No. 4405643 does not clarify the relationship between the alloy composition and detection sensitivity of an electrode. In the invention disclosed in Japanese Patent No. 4914447, the concentration of a gas component is determined on the premise that both the first electrode and the second electrode have a catalytic activity, although there may be a slight difference.

Japanese Patent No. 3566089 discloses or suggests nothing about a mixed-potential gas sensor including a sensing electrode formed as a single-layer cermet electrode (needless to say, about disabling of its sensing electrode as well). Japanese Patent No. 5323752 discloses that a pumping electrode for a limiting current gas sensor is made of Pt—Au alloy such that a Au abundance ratio is 0.01 or more and 0.3 or less, thereby increasing the selective decomposition ability for oxygen in the pumping electrode. Japanese Patent No. 5323752 also discloses that a Au abundance ratio exceeding 0.3 is not preferable because such a ratio increases electrode impedance. Japanese Patent No. 5323752, however, discloses or suggests nothing about a mixed-potential gas sensor (needless to say, about its sensing electrode as well).

The concentration of a hydrocarbon gas of an exhaust gas discharged during a normal operation (during a steady operation) of a typical diesel engine is on the order of 2000 ppmC at most (ppmC represents parts per million of capacity ratio in terms of carbon, which holds true for the following). Therefore, it is also considered that such a gas sensor is sufficient that can measure the concentration of a hydrocarbon gas in the range of up to approximately 2000 ppmC.

However, when a fuel is sprayed intentionally for the process of regenerating a diesel particulate filter (DPF) or when an injector for fuel injection goes out of order, a hydrocarbon gas may be discharged at a concentration greatly exceeding 2000 ppmC, for example, 4000 ppmC or more. This leads to a need for a gas sensor capable of accurately measuring the concentration of a hydrocarbon gas also in such a high concentration range.

However, the measurement range of the concentration of a hydrocarbon gas by the gas sensors disclosed in Japanese Patent Nos. 4405643 and 3566089 is approximately 2000 ppmC at most, and such a gas sensor cannot meet the need described above. Japanese Patent No. 4914447 merely discloses an example of measuring ammonia in the range of not more than 900 ppm and describes nothing about hydrocarbon, further, carbon monoxide.

SUMMARY OF THE INVENTION

The present invention relates to a gas sensor for sensing a predetermined gas component of a measurement gas, and more particularly, to a sensing electrode of the gas sensor.

According to the present invention, a mixed-potential gas sensor for measuring a concentration of a predetermined gas component of a measurement gas includes a sensor element mainly made of an oxygen-ion conductive solid electrolyte, a sensing electrode located on a surface of the sensor element, and a reference electrode including a cermet including Pt and an oxygen-ion conductive solid electrolyte. The sensing electrode includes a cermet including a noble metal and an oxygen-ion conductive solid electrolyte. The noble metal includes Pt and Au. A Au abundance ratio, which is an area ratio of a portion covered with the Au to a portion at which the Pt is exposed in a surface of noble metal particles forming the sensing electrode, is 0.1 or more and less than 0.3. The gas sensor determines a concentration of the predetermined gas component based on a potential difference between the sensing electrode and the reference electrode.

According to the present invention, a gas sensor capable of measuring the concentration of an unburned hydrocarbon gas in a range as high as 8000 to 16000 ppmC can be achieved.

The present invention therefore has an object to provide a gas sensor capable of accurately measuring a concentration of a target gas component in a concentration range higher than a conventional concentration range.

BRIEF DESCRIPTION OF THE DRAWINGS

FIGS. 1A and 1B are sectional views schematically illustrating an example configuration of a gas sensor according to a first configuration;

FIGS. 2A and 2B are sectional views schematically illustrating an example configuration of a gas sensor that is a modification according to the first configuration;

DESCRIPTION OF THE PREFERRED EMBODIMENTS

First Configuration

Figure 3A:
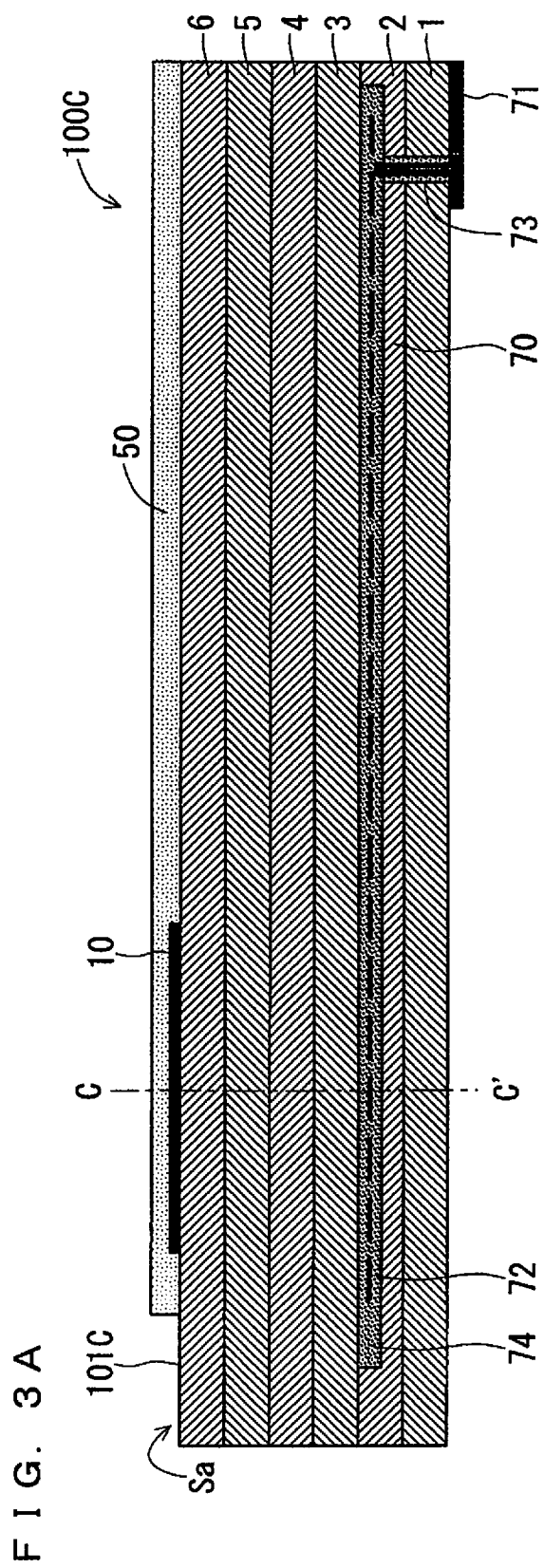
FIGS. 3A and 3B are sectional views schematically illustrating an example configuration of a gas sensor according to a second configuration.

FIGS. 1A and 1B are schematic sectional views schematically illustrating an example configuration of a gas sensor 100A according to a first configuration of the present invention. FIG. 1A is a vertical sectional view of a sensor element 101A that is a main component of the gas sensor 100A, which is taken along the longitudinal direction of the sensor element 101A. FIG. 1B is a view including a cross-section of the sensor element 101A perpendicular to the longitudinal direction of the sensor element 101A at a position A-A' of FIG. 1A.

The gas sensor 100A according to the first configuration of the present invention is a so-called mixed-potential gas sensor. Generally speaking, the gas sensor 100A determines the concentration of a gas component, which is a measurement target, of a measurement gas using a potential difference that occurs between a sensing electrode 10, which is provided on the surface of the sensor element 101A mainly made of ceramic being an oxygen-ion conductive solid electrolyte such as zirconia ($ZrO_2$), and a reference electrode 20, which is provided inside the sensor element 101A, due to a difference in the concentration of the gas component between the portions near the electrodes based on the principle of mixed potential.

More specifically, the gas sensor 100A preferably determines the concentration of a predetermined gas component of a measurement gas, where the measurement gas is an exhaust gas present in an exhaust pipe of an internal combustion engine such as a diesel engine or a gasoline engine. In this specification, description will be given of an example case where a predetermined gas component being a measurement target is an unburned hydrocarbon gas. In such a case, examples of the unburned hydrocarbon gas include carbon monoxide (CO) in addition to typical hydrocarbon gases (gases classified as hydrocarbons in terms of chemical formula) such as $C_2H_4$, $C_3H_6$, and n-C8. In the presence of a plurality of unburned hydrocarbon gases in a measurement gas, a potential difference occurring between the sensing electrode 10 and the reference electrode 20 has a value reflecting all the plurality of unburned hydrocarbon gases, and thus, a concentration value to be determined is also a total sum of the concentrations of the plurality of unburned hydrocarbon gases.

The sensor element 101A mainly includes a reference gas introduction layer 30, a reference gas introduction space 40, and a surface protective layer 50 in addition to the sensing electrode 10 and the reference electrode 20.

In the first configuration of the present invention, the sensor element 101A has the structure in which six layers, namely, a first solid electrolyte layer 1, a second solid electrolyte layer 2, a third solid electrolyte layer 3, a fourth solid electrolyte layer 4, a fifth solid electrolyte layer 5, and a sixth solid electrolyte layer 6, each formed of an oxygen-ion conductive solid electrolyte, are laminated in the stated order from the bottom side of FIGS. 1A and 1B. The sensor element 101A additionally includes other components mainly between these layers or on an outer peripheral surface of the element. The solid electrolytes constituting these six layers are fully airtight. Such a sensor element 101A is manufactured by, for example, laminating ceramic green sheets corresponding to the individual layers that have been subjected to a predetermined process and printing of a circuit pattern, and further, by integrating the laminated layers through firing.

The gas sensor 100A does not necessarily need to include the sensor element 101A formed of such a laminated body including the six layers. The sensor element 101A may be formed as a laminated body having more or fewer layers or may not have a laminated structure.

In the following description, for convenience' sake, the surface that is located as the upper surface of the sixth solid electrolyte layer 6 in FIGS. 1A and 1B is referred to as a front surface Sa of the sensor element 101A, and the surface that is located as the lower surface of the first solid electrolyte layer 1 in FIGS. 1A and 1B is referred to as a rear surface Sb of the sensor element 101A. In the determination of the concentration of the unburned hydrocarbon gas in a measurement gas with the gas sensor 100A, a predetermined range starting from a distal end E1 being one end of the sensor element 101A including at least the sensing electrode 10 is disposed in a measurement gas atmosphere; the other portion including a base end E2 opposite to the distal end E1 is disposed so as not to be in contact with the measurement gas atmosphere.

The sensing electrode 10 is an electrode for sensing a measurement gas. The sensing electrode 10 is formed as a porous cermet electrode made of Pt containing a predetermined ratio of Au, namely, Pt—Au alloy and zirconia. The sensing electrode 10 is provided at a position closer to the distal end E1 that is one end in the longitudinal direction of the sensor element 101A on the front surface Sa of the sensor element 101A. The sensing electrode 10 is provided in a substantially rectangular shape in plan view. The gas sensor 100A is placed such that, in its use, the sensor element 101A corresponding to at least the portion in which the sensing electrode 10 is provided is exposed to a measurement gas.

The catalytic activity of the sensing electrode 10 against an unburned hydrocarbon gas is disabled in its predetermined concentration range by preferably determining the composition of the Pt—Au alloy being its constituent material. That is, the decomposition reaction of an unburned hydrocarbon gas is inhibited in the sensing electrode 10. In the gas sensor 100A, accordingly, the potential of the sensing electrode 10 selectively varies with respect to (has correlation with) the unburned hydrocarbon gas, in accordance with its concentration. In other words, the sensing electrode 10 is provided in its respective concentration range so as to have high dependence of potential on concentration for an unburned hydrocarbon gas while having low dependence of potential on concentration for components of other measurement gas.

More specifically, in the sensor element 101A of the gas sensor 100A according to the first configuration of the present invention, the Au abundance ratio on the surface of the Pt—Au alloy forming the sensing electrode 10 is preferably determined, so that the sensing electrode 10 exhibits a remarkable dependence of potential on concentration in a concentration range of approximately 8000 to 16000 ppmC. Though described below in detail, this means that the sensing electrode 10 is provided to preferably sense an unburned hydrocarbon gas in a concentration range of 8000 to 16000 ppmC.

In this specification, the Au abundance ratio means an area ratio of the portion covered with Au to the portion at which Pt is exposed in the surface of the noble metal particles constituting the sensing electrode 10. In this specification, a Au abundance ratio is calculated from a peak intensity of a peak detected for Au and Pt, obtained using X-ray photoelectron spectroscopy (XPS), by a relative sensitivity coefficient method. The Au abundance ratio is 1 when the area of the portion at which Pt is exposed is equal to the area of the portion covered with Au.

The sensing electrode 10 will be described below in detail.

The reference electrode 20 is an electrode having a substantially rectangular shape in plan view, which is provided inside the sensor element 101A and serves as a reference in the determination of the concentration of the measurement gas. The reference electrode 20 is provided as the porous cermet electrode of Pt and zirconia.

It suffices that the reference electrode 20 has a porosity of 10% or more and 30% or lower and a thickness of 5 µm or more and 15 µm or less. The plane size of the reference electrode 20 may be smaller than that of the sensing electrode 10 as illustrated in FIGS. 1A and 1B, or may be equal to that of the sensing electrode 10 as in the second configuration described below (see FIGS. 3A and 3B).

The reference gas introduction layer 30 is a layer made of porous alumina and is provided inside the sensor element 101A to cover the reference electrode 20. The reference gas introduction space 40 is an internal space provided near the base end E2 of the sensor element 101A. Air (oxygen), serving as a reference gas in the determination of the concentration of an unburned hydrocarbon gas, is externally introduced into the reference gas introduction space 40.

The reference gas introduction space 40 and the reference gas introduction layer 30 are in communication with each other, and accordingly, in the use of the gas sensor 100A, the surroundings of the reference electrode 20 are always filled with air (oxygen) through the reference gas introduction space 40 and the reference gas introduction layer 30. During the use of the gas sensor 100A, thus, the reference electrode 20 always has a constant potential.

The reference gas introduction space 40 and the reference gas introduction layer 30 are provided so as not to come into contact with a measurement gas owing to their surrounding solid electrolytes. This prevents the reference electrode 20 from coming into contact with the measurement gas even when the sensing electrode 10 is exposed to the measurement gas.

In the case illustrated in FIGS. 1A and 1B, the reference gas introduction space 40 is provided in such a manner that part of the fifth solid electrolyte layer 5 is in communication with the exterior on the base end E2 of the sensor element 101A. The reference gas introduction layer 30 is provided so as to extend in the longitudinal direction of the sensor element 101A between the fifth solid electrolyte layer 5 and the sixth solid electrolyte layer 6. The reference electrode 20 is provided under the center of gravity of the sensing electrode 10 with reference to FIGS. 1A and 1B.

The surface protective layer 50 is a porous layer made of alumina, which is provided so as to cover at least the sensing electrode 10 on the front surface Sa of the sensor element 101A. The surface protective layer 50 is provided as an electrode protective layer that prevents or reduces the degradation of the sensing electrode 10 due to continuous exposure to a measurement gas during the use of the gas sensor 100A. In the case illustrated in FIGS. 1A and 1B, the surface protective layer 50 is provided so as to cover not only the sensing electrode 10 but also substantially the entire front surface Sa of the sensor element 101A except for a predetermined range starting from the distal end E1.

As illustrated in FIG. 1B, the gas sensor 100A is equipped with a potentiometer 60 capable of measuring a potential difference between the sensing electrode 10 and the reference electrode 20. Although FIG. 1B schematically illustrates wiring of the sensing electrode 10, the reference electrode 20, and the potentiometer 60, in an actual sensor element 101A, connection terminals (not shown) are provided correspondingly to the respective electrodes on the front surface Sa or the rear surface Sb on the base end E2 side, and wiring patterns (not shown), which connect the respective electrodes and their corresponding connection terminals, are formed on the front surface Sa and inside the element. The sensing electrode 10 and the reference electrode 20 are electrically connected with the potentiometer 60 via the wiring patterns and the connection terminals. Hereinbelow, a potential difference between the sensing electrode 10 and the reference electrode 20, which is measured by the potentiometer 60, is also referred to as a first sensor output.

The sensor element 101A further includes a heater part 70 that performs temperature control of heating the sensor element 101A and maintaining the temperature of the sensor element 101A, to enhance the oxygen ion conductivity of the solid electrolyte. The heater part 70 includes a heater electrode 71, a heater 72, a through hole 73, a heater insulating layer 74, and a pressure diffusion hole 75.

The heater electrode 71 is an electrode formed while being in contact with the rear surface Sb of the sensor element 101A (in FIGS. 1A and 1B, the lower surface of the first solid electrolyte layer 1). The heater part 70 can be powered externally through the heater electrode 71 connected with an external power supply (not shown).

The heater 72 is an electric resistor provided inside the sensor element 101A. The heater 72 is connected with the heater electrode 71 through the through hole 73 and generates heat by being powered externally via the heater electrode 71 to heat the solid electrolytes forming the sensor element 101A and maintain their temperatures.

In the case illustrated in FIGS. 1A and 1B, the heater 72 is buried while being vertically sandwiched between the second solid electrolyte layer 2 and the third solid electrolyte layer 3 so as to extend from the base end E2 to the position below the sensing electrode 10 near the distal end E1. This enables the adjustment of the entire sensor element 101A to the temperature at which the solid electrolytes are activated.

The heater insulating layer 74 is an insulating layer formed of an insulator such as alumina on the upper and lower surfaces of the heater 72. The heater insulating layer 74 is formed for electrical insulation between the second solid electrolyte layer 2 and the heater 72 and for electrical insulation between the third solid electrolyte layer 3 and the heater 72.

The pressure diffusion hole 75 is a part provided to penetrate the third solid electrolyte layer 3 and the fourth solid electrolyte layer 4 and to be in communication with the reference gas introduction space 40, and is formed to mitigate an internal pressure rise associated with a temperature rise in the heater insulating layer 74.

In the determination of the concentration of an unburned hydrocarbon gas in a measurement gas using the gas sensor 100A having such a configuration, as described above, the sensor element 101A in only a predetermined range, which starts from the distal end E1 and includes at least the sensing electrode 10, is disposed in a space containing a measurement gas, whereas the sensor element 101A on the base end E2 is apart from the space. And then, air (oxygen) is supplied to the reference gas introduction space 40. The heater 72 heats the sensor element 101A to an appropriate temperature from 400° C. to 800° C., preferably from 500° C. to 700° C., more preferably from 500° C. to 600° C.

In such a state, a potential difference occurs between the sensing electrode 10 exposed to the measurement gas and the reference electrode 20 exposed to the air. As described above, however, the potential of the reference electrode 20 disposed in the air (having a constant oxygen concentration) atmosphere is maintained at a constant potential, whereas the potential of the sensing electrode 10 selectively has a dependence on concentration for the unburned hydrocarbon gas of the measurement gas. The potential difference (sensor output) is thus substantially a value according to the composition of the measurement gas present around the sensing electrode 10. Therefore, a certain functional relationship (referred to as sensitivity characteristics) holds between the concentration of the unburned hydrocarbon gas and the sensor output. In the description below, such sensitivity characteristics may also be referred to as, for example, sensitivity characteristics for the sensing electrode 10.

In the actual determination of the concentration of an unburned hydrocarbon gas, in advance, a plurality of different mixed gases, each of which has a known concentration of an unburned hydrocarbon gas, are used as the measurement gas, and the sensitivity characteristics are experimentally identified by performing a measurement on the sensor output for each measurement gas. In the actual use of the gas sensor 100A, accordingly, an operation processor (not shown) converts the sensor output, which varies from moment to moment in accordance with the concentration of an unburned hydrocarbon gas in a measurement gas, into the concentration of the unburned hydrocarbon gas based on the sensitivity characteristics. The concentration of the unburned hydrocarbon gas in the measurement gas can thus be determined almost in real time.

Modification of First Configuration

FIGS. 2A and 2B are schematic sectional views schematically illustrating an example configuration of a gas sensor 100B, which is a modification of the gas sensor 100A. FIG. 2A is a vertical sectional view of a sensor element 101B, which is a main component of the gas sensor 100B, taken along the longitudinal direction of the gas sensor 100B. FIG. 2B is a view including a cross-section of the sensor element 101B perpendicular to the longitudinal direction of the sensor element 101B at a position B-B' of FIG. 2A.

The gas sensor 100B is provided in such a manner that the reference gas introduction space 40 of the sensor element 101A of the gas sensor 100A is extended to below the sensing electrode 10, whereas the reference gas introduction layer 30 is omitted and the reference electrode 20 is exposed to the reference gas introduction space 40. The other configurational elements are similar to those of the gas sensor 100A. Thus, the way how a sensor output occurs is the same as in the case of the gas sensor 100A. In other words, the gas sensor 100B is a so-called mixed-potential gas sensor similarly to the gas sensor 100A.

The gas sensor 100B having the configuration as described above, which includes the sensor element 101B and has sensitivity characteristics determined in advance similarly to the gas sensor 100A, can determine the concentration of an unburned hydrocarbon gas in a measurement gas.

Second Configuration

Figure 3B:
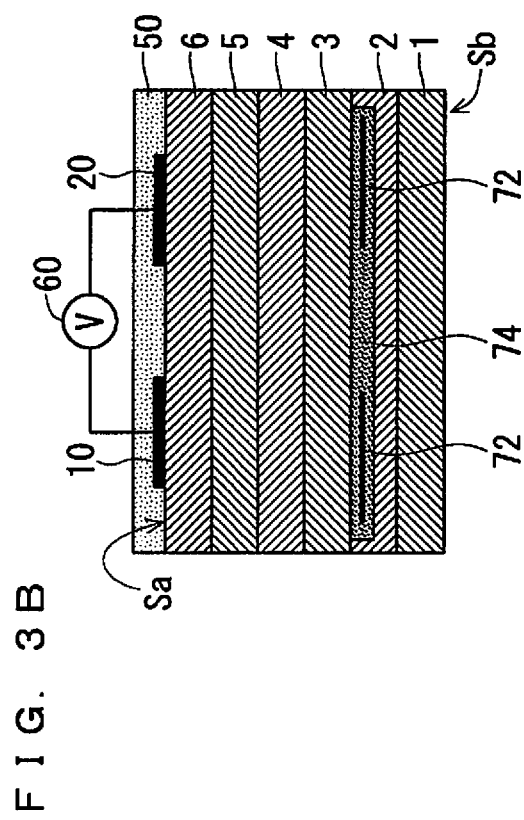

FIGS. 3A and 3B are schematic sectional views schematically illustrating a configuration example of a gas sensor 100C according to a second configuration of the present invention. FIG. 3A is a vertical sectional view of a sensor element 101C, which is a main component of the gas sensor 100C, taken along the longitudinal direction of the sensor element 101C. FIG. 3B is a view including a cross-section of the sensor element 101C perpendicular to the longitudinal direction of the sensor element 101C at a position C-C' of FIG. 3A.

The gas sensor 100C is also a so-called mixed-potential gas sensor similarly to the gas sensors 100A and 100B. In the sensor element 101C of the gas sensor 100C, however, not only the sensing electrode 10 but also the reference electrode 20 is disposed on the front surface Sa of the sensor element 101C and is covered with the surface protective layer 50, differently from the sensor element 101A and the sensor element 101B. The constituent materials for the respective electrodes of the gas sensor 100C are the same as those of the gas sensors 100A and 100B.

The gas sensor 100C includes no reference gas introduction space 40 (further, no reference gas introduction layer 30) and no pressure diffusion hole 75. The other components of the gas sensor 100C are similar to those of the gas sensors 100A and 100B. Although the sensing electrode 10 and the reference electrode 20 are provided at the same position in the longitudinal direction of the sensor element 101C (see FIG. 3B) in the case illustrated in FIGS. 3A and 3B, these electrodes may be disposed at different positions, for example, may be disposed in the longitudinal direction of the sensor element 101C.

In the determination of the concentration of an unburned hydrocarbon gas in a measurement gas using the gas sensor 100C having such a configuration, the sensor element 101C is disposed in such a manner that the reference electrode 20 as well as the sensing electrode 10 is exposed to the measurement gas, unlike the gas sensors 100A and 100B. Although the sensing electrode 10 and the reference electrode 20 are accordingly exposed to the same atmosphere, the constituent materials for the respective electrodes are the same as those for the gas sensors 100A and 100B. In the gas sensor 100C, thus, the potential of the sensing electrode 10 varies selectively with respect to the concentration of an unburned hydrocarbon gas as in the gas sensors 100A and 100B. On the other hand, unlike the sensing electrode 10, the catalytic activity of the reference electrode 20, which is formed as a porous cermet electrode of Pt and zirconia, is not prevented or reduced against a specific gas component. As a result, the sensing electrode 10 and the reference electrode 20 are identical in behavior toward gas components other than the unburned hydrocarbon gas. Thus, the sensor output of the gas sensor 100C substantially varies in accordance with an unburned hydrocarbon gas present in a measurement gas.

Similarly to the gas sensors 100A and 100B, thus, the gas sensor 100C whose sensitivity characteristics have been identified in advance can determine the concentration of an unburned hydrocarbon gas in a measurement gas.

Details of Sensing Electrode

As described above, in the gas sensors 100A to 100C, the sensing electrode 10 is formed so as to disable the catalytic activity against an unburned hydrocarbon gas in the predetermined concentration range. This is achieved by adding gold (Au) in addition to platinum (Pt) that is a main component to the sensing electrode 10 as their conductive components (noble metal components).

As the Au abundance ratio becomes higher, Au tends to become thicker on the surface of the noble metal particles forming the sensing electrode 10. More specifically, a Au-rich Pt—Au alloy tends to be formed near the surface of a Pt-rich Pt—Au alloy particle. As such a tendency becomes more conspicuous, the catalytic activity in the sensing electrode 10 is more likely to be disabled.

Figure 4:
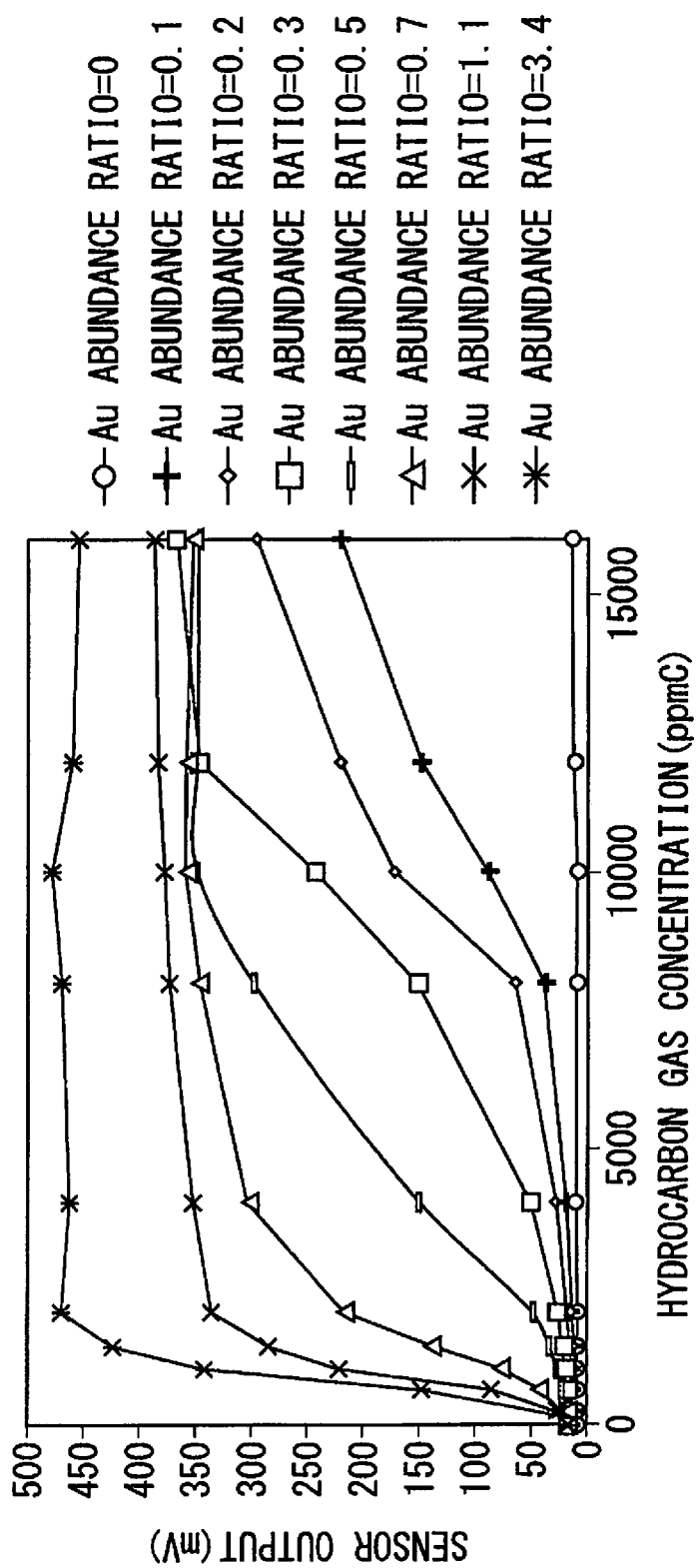
FIG. 4 is a graph illustrating sensitivity characteristics of eight types of sensor elements each having a different Au abundance ratio in a sensing electrode.

FIG. 4 is a graph illustrating the sensitivity characteristics (changes in sensor output with respect to the concentration of a hydrocarbon gas) in eight types of sensor elements 101A having different Au abundance ratios in the sensing electrodes 10. The measurement conditions for sensor output and the analysis conditions for Au abundance ratio when such sensitivity characteristics are obtained are as follows.

Measurement Conditions for Sensor Output

Element Control Temperature: 600° C.
Gas Atmosphere: $O_2$=10%, $H_2O$=5%, $C_2H_4$=200-16000 ppmC
Gas Flow Rate: 5 L/min
Pressure: 1 atm
Electrode Protective Layer: Porosity of 40%, 12 μm
Analysis Conditions for Au Abundance Ratio
Analyzer: X-ray Photoelectron Spectrometer (AXIS-HS from Simadzu/KRATOS Co.)
X-ray Source: Monochromatic Al
Tube Voltage, Tube Current: 15 kV, 15 mA
Lens Condition: Magnetic (analysis area of 120 um in diameter)
Resolution: Pass Energy 80
Scanning Rate: 200 eV/min (step of 1 eV)

FIG. 4 shows that in the case where the Au abundance ratio in the sensing electrode is zero (i.e., in the case where the metal component in the sensing electrode is Pt alone), the graph levels off, that is, no sensor output is obtained even at a high concentration of a hydrocarbon gas.

But, as the Au abundance ratio becomes higher from 0.1 to 0.2 to 0.3, the graph begins to slope gradually from the higher concentration side. An almost linear relationship is observed in the range of not less than 8000 ppmC for a Au abundance ratio of 0.1 and in the range of not less than 4000 ppmC for a Au abundance ratio of 0.2.

However, as the Au abundance ratio further becomes higher from 0.3 to 0.5 to 0.7 to 1.1 to 3.4, a sensor output is more likely to become saturated on the higher concentration side while the slope of the graph tends to become steeper on the lower concentration side. Specifically, for a Au abundance ratio of 0.3, although the graph slopes steeply in the range of not more than 12000 ppmC, the graph levels off in the range exceeding 12000 ppmC. For Au abundance ratios of 1.1 and 3.4, although the slope of the graph is steep in the range of not more than 2000 ppm, the sensor output becomes almost saturated in the range of not less than 2000 ppmC.

From the viewpoint of providing adequate measurement accuracy, it is empirically considered that the sensor output desirably changes with a rate of approximately 50 mV per 2000 ppmC. FIG. 4, however, shows that in the case of using the sensing electrode 10 whose Au abundance ratio is 0.3 or more, excellent measurement accuracy can be obtained in the range of not more than 12000 ppmC, but measurement accuracy is difficult to obtain in the range exceeding 12000 ppmC even for a Au abundance ratio of 0.3.

In the case of the sensing electrode 10 whose Au abundance ratio is 0.2, the sensor output value levels off at a value of almost zero in the range of not more than 8000 ppmC, but changes in sensor output per 2000 ppmC exceed approximately 50 mV at least up to 16000 ppmC in the range of not less than 8000 ppmC. This indicates that, in the case of using such a sensing electrode 10, the concentration of an unburned hydrocarbon gas can preferably be obtained from the sensor output in the range of not less than 8000 ppmC.

FIG. 4 also reveals that the concentration of an unburned hydrocarbon gas can be obtained preferably from a sensor output value in the range of at least 8000 to 16000 ppmC if the Au abundance ratio in the sensing electrode is 0.1.

Formed so as to measure the concentration of an unburned hydrocarbon in a concentration range as high as 8000 to 16000 ppmC by setting a Au abundance ratio in the sensing electrode 10 to 0.1 or more and less than 0.3, in consideration of such a relationship between the Au abundance ratio of the sensing electrode 10 and the sensitivity characteristics of the gas sensor, are the gas sensors 100A to 100C. Preferably, setting a Au abundance ratio in the sensing electrode 10 to 0.1 or more and 0.2 or less enables the gas sensors 100A to 100C to sense an unburned hydrocarbon gas more accurately in a concentration range of 8000 to 16000 ppmC than in any other concentration range.

The conceivable reason why the dependence of sensor output on concentration becomes remarkable on the higher concentration side in the case where the Au abundance ratio is small and the dependence of sensor output on concentration becomes remarkable on the lower concentration side in the case where the Au abundance ratio is large as illustrated in FIG. 4 is as follows: in the former case, unburned hydrocarbon of an exhaust gas burns due to the Pt catalytic activity before the unburned hydrocarbon reaches a three-phase interface to cause an electrochemical reaction, because of a high concentration of Pt in the sensing electrode 10, whereas in the latter case, part of the unburned hydrocarbon of the exhaust gas does not burn but reaches the three-phase interface in the form of an unburned hydrocarbon, thus causing an electrochemical reaction to produce a potential.

It suffices that the volume ratio between a noble metal component and zirconia of the sensing electrode 10 is approximately from 4:6 to 8:2.

For the gas sensors 100A to 100C to preferably exhibit their functions, the sensing electrode 10 preferably has a porosity of 10% or more and 30% or less and a thickness of 5 μm or more.

The plane size of the sensing electrode 10 may be appropriately determined, and it suffices that, for example, the length in the longitudinal direction of the sensor element is approximately 2 to 10 mm and the length in the direction perpendicular to the longitudinal direction is approximately 1 to 5 mm.

Outline of Process of Manufacturing Sensor Element

Next, the process of manufacturing the sensor elements 101A to 101C will be described using an example case where these sensor elements have the layer structures as illustrated in FIGS. 1A, 1B, 2A, 2B, 3A, and 3B. Generally speaking, the sensor elements 101A to 101C as illustrated in FIGS. 1A, 1B, 2A, 2B, 3A, and 3B are each manufactured by forming a laminated body formed of green sheets containing an oxygen-ion conductive solid electrolyte such as zirconia as a ceramic component and by cutting and firing the laminated body. The oxygen-ion conductive solid electrolyte may be, for example, yttrium partially stabilized zirconia (YSZ).

Figure 5:
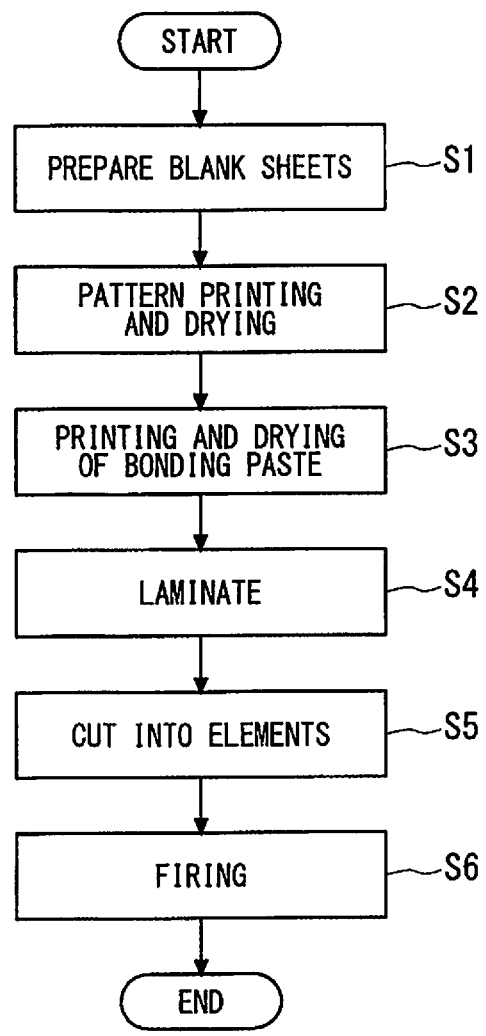
FIG. 5 is a flowchart illustrating a process of manufacturing the sensor element.

FIG. 5 is a flowchart illustrating the process of manufacturing the sensor elements 101A to 101C. In the manufacture of the sensor elements 101A to 101C, first, blank sheets (not shown) that are green sheets having no pattern formed thereon are prepared (step S1). Specifically, six blank sheets corresponding to the first to sixth solid electrolyte layers 1 to 6 are prepared. A blank sheet for forming the surface protective layer 50 is prepared as well. A plurality of sheet holes used for positioning in printing and lamination are provided in the blank sheets. Such sheet holes are formed in advance through, for example, punching with a punching machine. For a green sheet whose corresponding layer forms an internal space, a penetration corresponding to the internal space is also provided in advance through, for example, punching as described above. All the blank sheets corresponding to the respective layers of the sensor elements 101A to 101C need not to have the same thickness.

After the preparation of the blank sheets corresponding to the respective layers, pattern printing and drying are performed to form various patterns on the individual blank sheets (step S2). Specifically, electrode patterns of, for example, the sensing electrode 10 and the reference electrode 20, the reference gas introduction layer 30, internal wiring (not shown), and the like are formed. In the first solid electrolyte layer 1, a cut mark is printed that serves as a reference cut position when the laminated body is cut in a subsequent step.

Each pattern is printed by applying a paste for pattern formation, prepared in accordance with the characteristic required for each formation target, to the blank sheet by a known screen printing technique. Any known drying means is available for drying after printing.

The sensor elements 101A to 101C are characterized in the manner of preparing a conductive paste for use in the formation of the sensing electrode 10, which will be described below in detail.

After the pattern printing, printing and drying of a bonding paste are performed to laminate and bond the green sheets corresponding to the respective layers (step S3). Any known screen printing technique is available for printing of a bonding paste, and any known drying means is available for drying after printing.

Subsequently, crimping is performed in which the adhesive-applied green sheets are laminated in a predetermined order, and the laminated green sheets are crimped on the predetermined temperature and pressure conditions, to thereby form a laminated body (step S4). Specifically, green sheets that are lamination targets are laminated while being positioned at the sheet holes to be held in a predetermined lamination jig (not shown), and the green sheets together with the lamination jig are heated and pressurized by a lamination machine such as a known hydraulic pressing machine. The pressure, temperature, and time for heating and pressurizing depend on a lamination machine to be used, whose conditions may be set appropriately for good lamination.

After the laminated body has been obtained as described above, subsequently, a plurality of parts of the laminated body are cut out as individual units (referred to as element bodies) of the sensor elements 101A to 101C (step S5). The cut out element bodies are fired under predetermined conditions, thereby producing the sensor elements 101A to 101C as described above (step S6). In other words, the sensor elements 101A to 101C are produced by integrally firing the solid electrolyte layers and the electrodes. The firing temperature is preferably 1200° C. or higher and 1500° C. or lower (for example, 1400° C.). The integral firing performed in such a manner provides satisfactory adhesion strength to the respective electrodes of the sensor elements 101A to 101C.

The resultant sensor elements 101A to 101C are housed in a predetermined housing and incorporated into main bodies (not shown) of the gas sensors 100A to 100C.

Conductive Paste for Forming Sensing Electrode

Next, a conductive paste used to form the sensing electrode 10 will be described. The conductive paste for forming a sensing electrode is produced by using a Au ion-containing liquid as a Au starting material and mixing the Au ion-containing liquid with a Pt powder, a zirconia powder, and a binder. Any binder that can disperse any other row material to the printable extent and vanishes through firing may be appropriately selected. The production of a conductive paste in such a manner is referred to as liquid-state Au mixing.

Here, the Au ion-containing liquid is obtained by dissolving a salt containing Au ion or an organometallic complex containing Au ion in a solvent. The Au ion-containing salt may be, for example, tetrachloroauric(III) acid ($HAuCl_4$), sodium chloroaurate(III) ($NaAuCl_4$), or potassium dicyanoaurate(I) ($KAu(CN)_2$). The Au ion-containing organometallic complex may be, for example, gold(III) diethylenediamine trichloride ($[Au(en)_2]Cl_3$), gold(III) dichloro(1,10-phenanthroline)chloride ($[Au(phen)Cl_2]Cl$), dimethyl (trifluoroacetylacetonate)gold, or dimethyl (hexafluoroacetylacetonate)gold. Tetrachloroauric(III) acid or gold(III) diethylenediamine chloride ($[Au(en)_2]Cl_3$) is preferably used from the viewpoint of no impurity such as Na or K remaining in the electrode, easy handling, or dissolvability in the solvent. The solvent may be acetone, acetonitrile, or formamide as well as alcohols such as methanol, ethanol, and propanol.

Mixing can be performed by well-known means such as instillation. Although the obtained conductive paste contains Au present in ionic (complex ionic) state, the sensing electrodes 10 formed in the sensor elements 101A to 101C obtained through the above-mentioned manufacturing process contain Au mainly as an elemental metal or as an alloy with Pt.

Figure 6A:
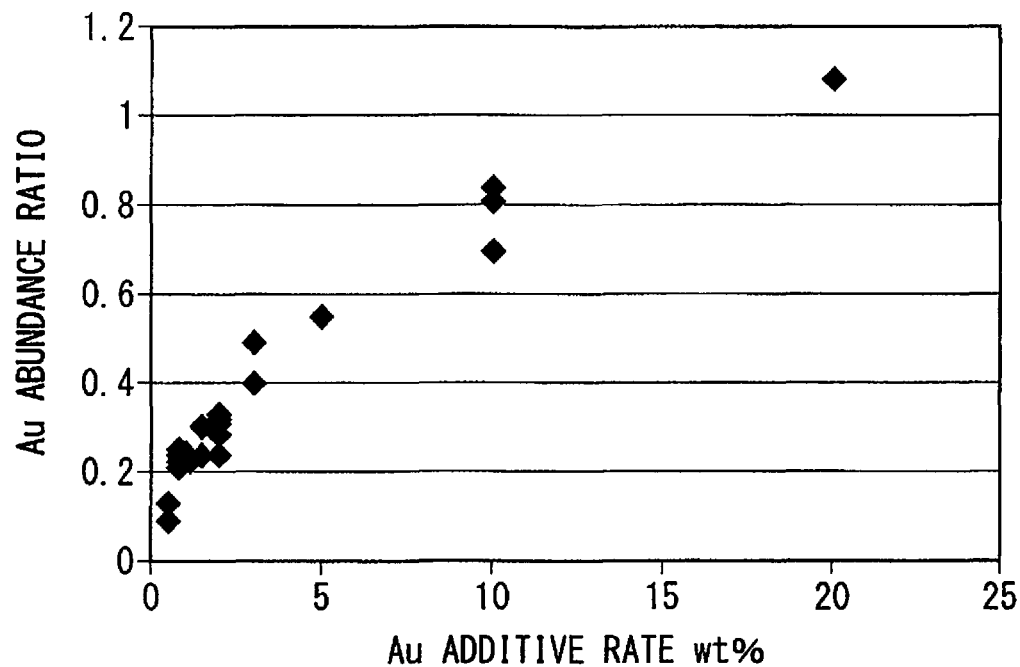
FIGS. 6A and 6B illustrate Au abundance ratios in a sensing electrode made of a conductive paste for the formation of a sensing electrode, which are plotted against Au additive rates, where the conductive paste is produced through liquid-state Au mixing.
Figure 6B:
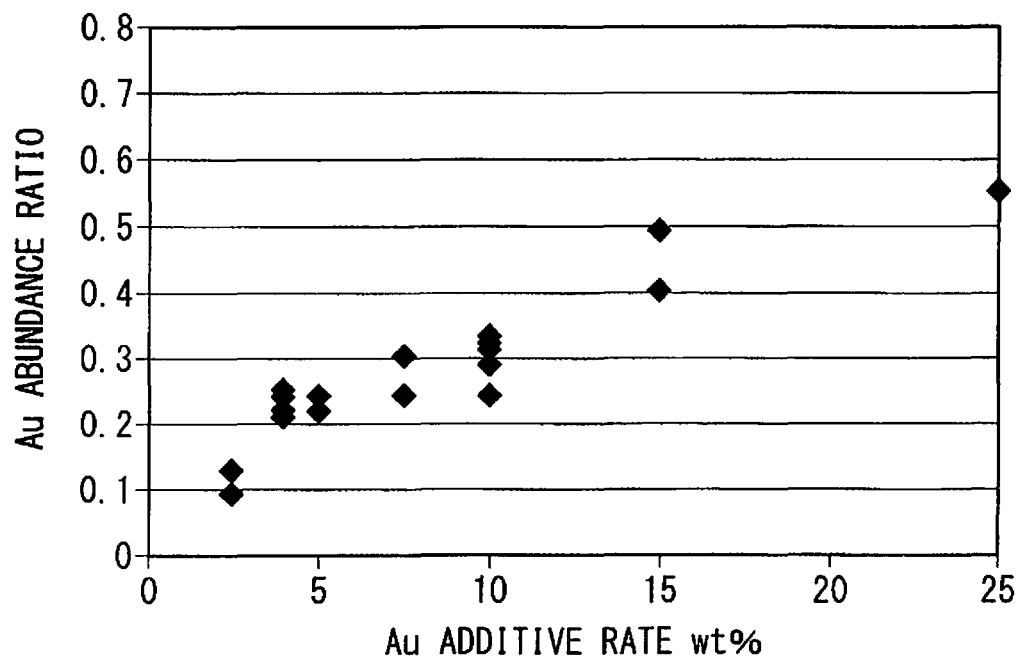

FIGS. 6A and 6B illustrate Au abundance ratios in the sensing electrode 10 formed of a conductive paste for forming a sensing electrode, which are plotted against Au weight ratios (hereinbelow, referred to as Au additive rates) with respect to the weight of all the noble metal elements (a total weight of Pt and Au) of a starting material, where the conductive paste is produced through liquid-state Au mixing. FIG. 6B is a partially-enlarged figure of FIG. 6A.

FIGS. 6A and 6B reveal that a Au abundance ratio tends to increase with a Au additive rate monotonously and that the sensing electrode 10 whose Au abundance ratio is 0.1 or more and less than 0.3 can be manufactured in the case where a Au additive rate is 0.5 wt % or more and less than 2 wt %. In other words, the use of a conductive paste whose Au additive rate is 0.5 wt % or more and less than 2 wt % preferably forms the sensing electrode 10 whose Au abundance ratio is 0.1 or more and less than 0.3.

Another Way of Producing Conductive Paste

In the production of a conductive paste for forming a sensing electrode, the conductive paste may be produced by using a coating powder, which is obtained by coating a Pt powder with Au, as a starting material, instead of producing the conductive paste through liquid-state Au mixing as described above. In such a case, a conductive paste for a sensing electrode is produced by mixing the coating powder, a zirconia powder, and a binder. Here, the coating powder used in the above production may be obtained by covering the particle surface of a Pt powder with a Au film or applying Au particles to Pt powder particles.

Also in this case, the sensing electrode 10 whose Au abundance ratio is 0.1 or more and less than 0.3 can preferably be formed.

Modifications

In the embodiments above, the sensing electrode 10 is formed such that a Au abundance determined based on the result of the XPS measurement is 0.1 or more and less than 0.3. Alternatively, a Au abundance ratio may be calculated based on the result of the auger electron spectroscopy (AES) measurement. In such a case, an indicator of the Au abundance ratio on the surface of a noble metal particle constituting the sensing electrode 10 may be an index value that is substantially equivalent to the Au abundance ratio on the surface of the sensing electrode used in the embodiments or may be an index value convertible into the Au abundance ratio. In auger electron spectroscopy analysis, a Au abundance ratio may be determined where the broken surface of a sensor element is an analysis target.

Although the embodiments above have described the cases in which the measurement gas is an exhaust gas present in an exhaust pipe of an internal combustion engine such as a diesel engine or a gasoline engine and the concentration of an unburned hydrocarbon gas in the measurement gas is determined, the measurement targets of the gas sensors 100A to 100C are not limited to a hydrocarbon gas. The gas sensors 100A to 100C can also measure the concentrations of $NH_3$ and NOx based on the principle of mixed potential as in the embodiments above.

What is claimed is:

1. A mixed-potential type hydrocarbon gas sensor that measures a concentration of a hydrocarbon gas of a measurement gas, said gas sensor comprising:
   a sensor element mainly made of an oxygen-ion conductive solid electrolyte;
   a sensing electrode for sensing said hydrocarbon gas, said sensing electrode provided on a surface of said sensor element; and
   a reference electrode including a cermet including Pt and an oxygen-ion conductive solid electrolyte;
   wherein:
   said sensing electrode includes a cermet comprising a plurality of noble metal particles and an oxygen-ion conductive solid electrolyte,
   said noble metal particles each comprise an alloy of Pt and Au,
   a Au abundance ratio, which is an area ratio of a portion covered with said Au to a portion at which said Pt is exposed in a surface of each of the plurality of noble metal particles, is 0.1 or more and less than 0.3, and
   said gas sensor is configured to determine the concentration of said hydrocarbon gas based on a potential difference between said sensing electrode and said reference electrode.

2. The gas sensor according to claim 1, further comprising an electrode protective layer that is a porous layer covering at least said sensing electrode.

3. The gas sensor according to claim 2, wherein said sensor element further includes a reference gas introduction space into which a reference gas is introduced, said reference gas introduction space separated from a space containing said measurement gas, and said reference electrode is placed in an atmosphere of said reference gas.

4. The gas sensor according to claim 2, wherein said sensing electrode and said reference electrode are disposed on the surface of said sensor element.

5. The gas sensor according to claim 4, wherein said sensing electrode and said reference electrode are covered with an electrode protective layer.

6. The gas sensor according to claim 1, wherein said sensor element further includes a reference gas introduction space into which a reference gas is introduced, said reference gas introduction space separated from a space containing said measurement gas, and said reference electrode is placed in an atmosphere of said reference gas.

7. The gas sensor according to claim 6, wherein said sensor element further includes a reference gas introduction layer that is a porous layer in communication with said reference gas introduction space, and said reference electrode is covered with said reference gas introduction layer.

8. The gas sensor according to claim 6, wherein said reference electrode is exposed to said reference gas introduction space.

9. The gas sensor according to claim 1, wherein said sensing electrode and said reference electrode are disposed on the surface of said sensor element.

10. The gas sensor according to claim 9, wherein said sensing electrode and said reference electrode are covered with said electrode protective layer.

11. A method for producing a conductive paste, said conductive paste being used to form a sensing electrode of a mixed-potential gas sensor for measuring a concentration of a predetermined gas component of a measurement gas, said method comprising the steps of:
    preparing a starting material; and
    mixing said starting material,
    wherein
    said starting material is prepared as
      a mixture of at least a Pt powder, an ion-containing liquid obtained by dissolving a salt or an organometallic complex containing a Au ion in a solvent, a zirconia powder, and a binder, or
      a mixture of at least a coating powder containing a Pt powder coated with Au, a zirconia powder, and a binder,
    said starting material is mixed such that a weight ratio of said Au in a noble metal component of said conductive paste is 0.5 wt % or more and less than 2 wt %, said gas sensor comprises
- a sensor element mainly made of an oxygen-ion conductive solid electrolyte,
- a sensing electrode located on a surface of said sensor element, and
- a reference electrode including a cermet including Pt and an oxygen-ion conductive solid electrolyte, said sensing electrode includes a cermet comprising a plurality of noble metal particles and an oxygen-ion conductive solid electrolyte, said noble metal particles each comprise an alloy of Pt and Au, a Au abundance ratio, which is an area ratio of a portion covered with said Au to a portion at which said Pt is exposed in a surface of each of the plurality of noble metal particles, is 0.1 or more and less than 0.3, and said gas sensor determines a concentration of said predetermined gas component based on a potential difference between said sensing electrode and said reference electrode.

12. A method for manufacturing a gas sensor, said method comprising:
(a) preparing a conductive paste;
(b) preparing a plurality of green sheets each comprising an oxygen-ion conductive solid electrolyte;
(c) applying said conductive paste to some of said plurality of green sheets to form a pattern of said sensing electrode;
(d) forming a laminated body of said plurality of green sheets including the green sheets on which the pattern of said sensing electrode has been formed; and
(e) firing said laminated body to integrally fire said sensing electrode with said solid electrolyte,
wherein
said step (a) comprises the steps of
(a-1) preparing a starting material, and
(a-2) mixing said starting material, said starting material is prepared as
- a mixture of at least a Pt powder, an ion-containing liquid obtained by dissolving a salt or an organometallic complex containing a Au ion in a solvent, a zirconia powder, and a binder, or
- a mixture of a coating powder containing a Pt powder coated with Au, a zirconia powder, and a binder, said starting material is mixed such that a weight ratio of said Au in a noble metal component of said conductive paste is 0.5 wt % or more and less than 2 wt %, said gas sensor comprises
- a sensor element mainly made of an oxygen-ion conductive solid electrolyte,
- a sensing electrode located on a surface of said sensor element, and
- a reference electrode including a cermet including Pt and an oxygen-ion conductive solid electrolyte, said sensing electrode includes a cermet comprising a plurality of noble metal particles and an oxygen-ion conductive solid electrolyte, said noble metal particles each comprise an alloy of Pt and Au, a Au abundance ratio, which is an area ratio of a portion covered with said Au to a portion at which said Pt is exposed in a surface of each of the plurality of noble metal particles, is 0.1 or more and less than 0.3, and said gas sensor determines a concentration of said predetermined gas component based on a potential difference between said sensing electrode and said reference electrode.

* * * * *